United States Patent [19]

Gorman et al.

[11] Patent Number: 4,492,759

[45] Date of Patent: Jan. 8, 1985

[54] FIELD-TEST METHOD AND APPARATUS FOR THE DETECTION OF ASBESTOS

[75] Inventors: Esther M. Gorman; William W. Gorman, Jr., both of St. Petersburg Beach, Fla.

[73] Assignee: E-C Apparatus Corporation, St. Petersburg, Fla.

[21] Appl. No.: 334,591

[22] Filed: Dec. 28, 1981

[51] Int. Cl.³ .............................................. G01N 31/22
[52] U.S. Cl. ...................................... 436/72; 422/61; 422/101; 422/102; 436/79; 436/84; 436/177
[58] Field of Search ..................... 436/72, 79, 84, 182, 436/177, 178; 422/61, 101, 102

[56] References Cited

U.S. PATENT DOCUMENTS 3,215,500 11/1965 Bittner .................................. 436/177
3,881,822 5/1975 Rose ...................................... 436/72

OTHER PUBLICATIONS

Kim et al., Test for Screening Asbestos NIOSH, No. 80-110 1979.

*Primary Examiner*—Michael S. Marcus
*Attorney, Agent, or Firm*—Bernard, Rothwell & Brown

[57] ABSTRACT

An improved field-test method and apparatus for the detection of asbestos by detecting magnesium or iron is described wherein all of the reactions of the test are performed in one reaction tube or column. The method includes the steps of placing a sample in the tube, washing the sample in the tube, adding acid reagent to the sample, and adding a color reagent to the sample in the tube to indicate qualitatively if asbestos is present in the sample. The apparatus is in the form of a compact kit containing multiple columns with caps and other labware needed for the test.

6 Claims, 4 Drawing Figures

FIELD-TEST METHOD AND APPARATUS FOR THE DETECTION OF ASBESTOS

FIELD OF THE INVENTION

This invention pertains to an improved method and test kit for field-testing to detect asbestos.

DESCRIPTION OF THE PRIOR ART

Asbestos is thought to present a significant health hazard to humans, particularly when it is airborne. Even solid asbestos, found in a variety of construction materials, may be made airborne by mechanical disruption. There has therefore been interest in detecting asbestos in solid form to identify the source of potential health problems. The presence of asbestos may be established with a variety of techniques including optical microscopy, polarized light microscopy, electron optical microscopy, X-ray refractometry, infra-red spectrotometry, thermal analysis and elemental analysis. Many of these tests employ expensive equipment that requires extensive skill to operate. Before resorting to elaborate detection methods an inexpensive field-test may be used to quickly determine whether asbestos is likely to be present. If the field-test is positive, more accurate and elaborate testing may be conducted to positively establish the presence or absence of asbestos.

Such field-tests rely on the fact that asbestos contains certain quantities of either magnesium and/or iron. Approximately 90% of the asbestos used in the world contains magnesium without iron while the other 10% contains iron with or without magnesium. Magnesium is known to produce a characteristic blue color in the presence of certain reagents and iron is known to produce a characteristic reddish color in the presence of certain reagents. A field-test or screening-test for the detection of asbestos which takes advantage of the color development characteristics of magnesium and iron is described by Walter S. Kim, James W. Carter II, and Richard E. Couple in an article entitled "Quick Screening Test for Asbestos", Am. Ind. Hyg. Assoc., March 1981, pp. 198–201. Since Magnesium is present in most asbestos its presence is tested for first, and the iron test is conducted only if the magnesium test is negative.

The procedure described by Kim et al. to test for magnesium bearing asbestos requires washing the sample to be tested with glycerine in a first vessel, such as a beaker. The material in the beaker is filtered through a cellulose ester filter contained in a separate filtration vessel. After the test material is washed thoroughly it is removed from the filter paper and placed in a third vessel, such as a dish, for color development. In the dish the remaining sample is reacted with acids and finally a reagent for color development. If a blue color develops upon addition of a magnesium reagent, asbestos might be present and the sample may be sent to a laboratory for confirmation using a more elaborate test.

If the magnesium test is negative, the sample should then be tested for the presence of iron. The process for testing for iron described by Kim et al. requires that the sample initially be washed in a first vessel with an acetic-sulfuric acid mixture rather than glycerin. The sample is then transferred to a second vessel for filtration using a cellulose ester filter paper. The material remaining on the paper filter is transferred again to a separate dish where a drop of hydrofluoric acid solution is added to the sample. The iron reagent is then added for color development. If a reddish color develops asbestos might be present and the sample may be sent to a laboratory for confirmation using more elaborate tests.

The repeated transfer of material from one vessel to another required by the procedure described by Kim et al. is cumbersome and the cellulose ester filter used in the filtration assembly may be ruptured easily by one unskilled in handling such equipment, resulting in the loss of important sample material. In addition, the acids required for this test are quite corrosive making it desirable to minimize the handling of the sample and the chemicals.

There is a need in the prior art for a qualitative test which is simple to perform, and provides minimum handling of the sample and the chemicals, which can be used as a field-test for asbestos, and which requires no complex instruments.

SUMMARY OF THE INVENTION

This invention provides a colorimetric qualitative test for the detection of asbestos by testing for magnesium and iron present in samples of asbestos. The method enables the magnesium and iron elemental analysis to be done in a single reaction column or tube using stepwise sample treatment by first washing away unwanted materials, then releasing magnesium and/or iron (if present) and reacting them with color reagents for visual detection. A sample kit containing all required labware and chemicals allows an unskilled worker to run the test, with no instrumentation required.

DETAILED DESCRIPTION OF THE INVENTION

Figure 1:
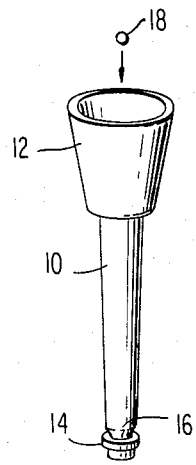
FIG. 1 illustrates a column used in this invention before a sample is placed therein.

In FIG. 1, there is shown one embodiment of the apparatus in which the method of this invention is carried out. A reaction tube or column 10 is illustrated in which a sample to be tested is placed and all of the steps involved in the present invention are conducted without transferring the material to be tested to another vessel to prevent spillage of fluids used in the test. A cap 14 adapted to detachedly fix over and seal one end of the column is also provided. Filter material 16 is lodged at the lower end of the column.

Figure 4:
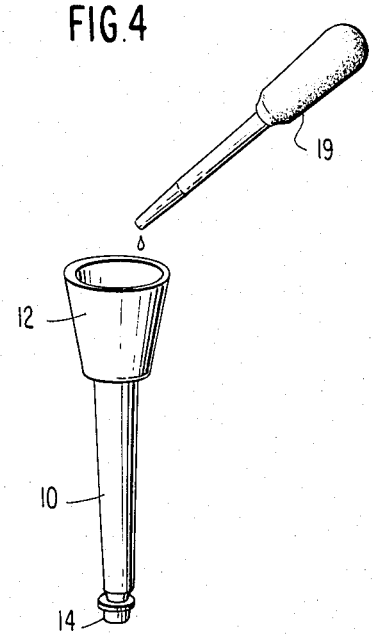
FIG. 4 illustrates a column used in this invention during reaction of the sample with chemicals and color development steps.

Before conducting a test for the presence of asbestos, the column may be marked with a wax pencil or other indicating means so the test results may be preserved. At the beginning of the test, the funnel 12 is preferably attached to the upper end of the column 10 and the cap 14 is attached to the lower end. An unknown sample 18 is then dropped into the column. Since magnesium is present in most commonly used asbestos, the test for the presence of magnesium bearing material is usually performed first. For this test, several drops of glycerin are added to the sample in the column, e.g., by a dropper 19 as illustrated in FIG. 4. The glycerin releases any magnesium not associated with asbestos (unbound). The released unbound non-asbestos magnesium ions are washed away by distilled water. It may be desirable to stir the sample and glycerine with a stir rod 20 to ensure thorough mixing.

Figure 2:
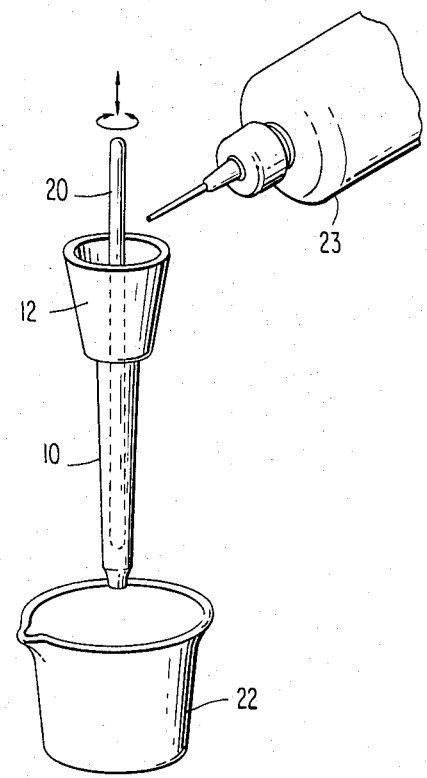
FIG. 2 illustrates a column used in this invention during filtration.
Figure 3:
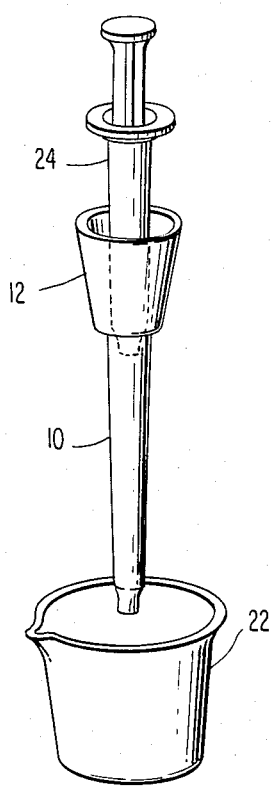
FIG. 3 illustrates a column used in this invention with a syringe for forcing liquid through the vessel.

After the sample has been mixed with the glycerin, the cap 14 may be removed with the column positioned over a beaker 22 which receives the excess liquid. To remove waste, the sample should then be washed with distilled water, e.g., from a bottle 23, shown in FIG. 2, allowing the excess fluid and waste to drain into the beaker. It may be necessary to apply force at the upper end of the column to force the water out of the column. This may be accomplished by any suitable means, but a syringe 24 adapted to fit into the column and to force air through the column has been found to be satisfactory. Further, it has been found most desirable to continue the washings until approximately 50 milliliters of distilled water have been collected in the beaker 22.

When the sample has been thoroughly washed, the cap 14 is again placed on the end of the column. Then a small amount of phosphoric acid, approximately 1 drop, is placed into the column through the funnel 12, see FIG. 4, and is mixed well by grinding the sample with the stirring rod 20. This releases the bound magnesium in the asbestos sample for further reaction. Next, five drops of sodium hydroxide, preferably 10N sodium hydroxide, is added to the column and mixed with the sample. For color complexing, five drops of magnesium color indicating reagent, 4-(p-nitrophenylazo) resorcinol, are then added to determine the presence or absence of magnesium. A blue color indicates that a magnesium bearing asbestos i.e., usually chrysotile type asbestos, may be present. The funnel may then be removed and a top cap (not shown) may be placed on the upper end of column 10. The column, now capped at both ends, may be preserved for future reference.

If the test for magnesium is negative, a different sample of the same material should be tested for the presence of iron to determine whether any iron bearing asbestos i.e., amosite or crocidolite asbestos, might be present. In conducting this test, five drops of acetic acid and five drops of sulfuric acid are placed in the column 10 and mixed with the sample by a stirring rod. This releases unbound non-asbestos iron. While the column is held over a beaker, the cap is removed to allow the acid to drain out of the column. The sample is then washed to remove waste with approximately 50 milliliters of distilled water, which may be collected in the beaker as before. A syringe or other suitable device again may be needed to force the water through the column. After approximately 50 milliliters of water has drained through the column into the beaker, the cap 14 is placed on the bottom of the column 10. One drop of hydrofluoric acid is then added to the sample in the column and mixed with the sample to release the bound asbestos iron for further reaction. After the hydroflouric acid and sample have been thoroughly mixed, several drops of an iron color reagent, 1, 10 Phenanthroline, is added to the column. If a reddish color develops an iron bearing form of asbestos may be present. To preserve the test sample, the funnel is removed and a top cap is placed on the column.

The column used for this test may be a variety of sizes but for field-test purposes it has been found most desirable to use a column approximately 3-4 inches long with a diameter at its upper end of between $\frac{1}{4}''$ and $\frac{1}{2}''$ with a gradual taper to the lower end where the filter material is lodged. This test has been found to be most reliable in situations where the samples contain at least 1% asbestos. The sample size may vary, but best results were obtained when the sample size was about $\frac{1}{4}''$ in diameter and approximately $\frac{1}{8}''$ thick. Thin samples are most desired for use with the illustrated apparatus since they will not plug the pores of the filter in the column and will also speed the test. The filter material is preferably made of polypropylene which is corrosion resistant against the alkali and acids used in the assays.

For the convenience of the user, the materials needed to perform the method of this invention may be provided in a kit. In general, the kit will include a number of columns with caps and funnels. A beaker, forceps, a small syringe, a Teflon stirring rod, a test tube rack and a wax pencil complete the labware requirements for the test. The kit should also provide the necessary chemicals for conducting the tests. For the magnesium tests, the chemicals required would include glycerin, phosphoric acid, 10N sodium hydroxide, and a magnesium color reagent. The magnesium color reagent is preferably 4-(p-nitrophenylazo) resorcinol. For the iron test, the chemicals to be supplied in the kit would include acetic acid, sulfuric acid, hydrofluoric acid and an iron indicating reagent. The iron indicating reagent is preferably 1, 10-phenanthroline. Each of the chemicals and distilled water would be supplied in separate bottles.

This invention provides a unique field-test which may be conducted in a single column or tube for the rapid identification of magnesium and iron found in the various forms of asbestos. The test is simple so that it can be run by unskilled labor to provide a quick assessment of whether asbestos may be present in material found in a particular location. The method of this invention requires no instrumentation, and the materials required can be supplied in a small kit containing labware and chemicals which can be stored for up to six months at normal ambient temperatures. The method of this invention minimizes the handling required of the materials needed to perform this field test, thereby reducing the risks to the personnel conducting the tests. In addition, the simplified procedures provided in this method enable unskilled persons to perform the test with a minimum of danger from the handling of the chemicals involved. The filter provided in the tube used in this invention is not easily broken permitting the tests to be conducted without loss of materials or time. Using the method and apparatus of this invention also provides the advantage of leaving the tested samples in a convenient capped column which may be stored for as long as the chemicals are stable for future reference and comparisons.

What is claimed is:

1. Step-by-step method for conducting field-tests for the possible presence of asbestos comprising the following sequentially performed steps:
    (a) placing a sample to be tested in an open column having removable top and bottom caps and a filter material resistant to phosphoric acid and sulfuric acid, the filter material being lodged inside the column, at one end;
    (b) preparing the sample in the same column for testing by washing said sample in the same column to remove waste;
    (c) draining the wash water and waste from the same column through said filter material leaving a residue to be tested on said filter material;
    (d) placing said bottom cap on said column;
    (e) reacting the residue on said filter material with an acid reagent for releasing magnesium or iron, by contacting the residue on said filter material with said acid reagent in the same column and with said bottom cap in place on said column; and (f) adding a color indicating reagent to the residue on said filter material and in the same column to detect the presence of magnesium or iron.

2. A method as defined in claim 1 wherein the reactant is mixed with the sample by stirring.

3. A method as defined in claim 1 further comprising capping the same column to close it after the test is completed and storing the capped column to retain the test results.

4. The method as defined in claim 1 wherein the steps are first performed with an acid reagent and color reagent for releasing and detecting magnesium, and if the results are negative, the steps are performed again with an acid reagent and color reagent for releasing and detecting iron.

5. A method as defined in claim 1 wherein the washing includes stirring distilled water in the column with the sample.

6. A method as defined in claims 1 and 5 wherein the water is flushed through the same column and filter material by inserting a syringe into the same column and forming a pressure seal.

* * * * *

UNITED STATES PATENT AND TRADEMARK OFFICE
CERTIFICATE OF CORRECTION

PATENT NO. : 4,492,759

DATED : January 8, 1985

INVENTOR(S) : Esther M. Gorman et al.

It is certified that error appears in the above-identified patent and that said Letters Patent is hereby corrected as shown below:

On the title page;
In paragraph [75] Inventors, line 3, after "Beach, Fla." insert -- William H. Lederer of Pittsburgh, Pa. --.

Column 6, Claim 5, line 2, after "the" and before "column" insert -- same --.

Signed and Sealed this

Twenty-fifth Day of June 1985

[SEAL]

Attest:

DONALD J. QUIGG

Attesting Officer     Acting Commissioner of Patents and Trademarks